United States Patent
Jegou

(10) Patent No.: US 8,753,615 B2
(45) Date of Patent: Jun. 17, 2014

(54) ETHYLENE COPOLYMER WITH PEG, CATIONIC AND ANIONIC UNITS, COSMETIC COMPOSITION INCLUDING SAME AND TREATMENT METHOD

(75) Inventor: Gwenaelle Jegou, Saint Michel sur Orge (FR)

(73) Assignee: L'Oreal, Paris (FR)

( * ) Notice: Subject to any disclaimer, the term of this patent is extended or adjusted under 35 U.S.C. 154(b) by 206 days.

(21) Appl. No.: 13/260,062

(22) PCT Filed: Mar. 11, 2010

(86) PCT No.: PCT/FR2010/050418
§ 371 (c)(1),
(2), (4) Date: Nov. 29, 2011

(87) PCT Pub. No.: WO2010/116063
PCT Pub. Date: Oct. 14, 2010

(65) Prior Publication Data
US 2012/0070399 A1 Mar. 22, 2012

Related U.S. Application Data

(60) Provisional application No. 61/169,003, filed on Apr. 14, 2009.

(30) Foreign Application Priority Data

Apr. 9, 2009 (FR) .................. 09 52339
Jul. 8, 2009 (FR) .................. 09 03356
Sep. 21, 2009 (FR) .................. 09 56455

(51) Int. Cl.
*A61K 8/00* (2006.01)
*A61K 8/81* (2006.01)
*A61Q 5/12* (2006.01)
*C08F 226/02* (2006.01)
*C08F 220/06* (2006.01)

(52) U.S. Cl.
CPC . *A61K 8/817* (2013.01); *A61Q 5/12* (2013.01); *C08F 226/02* (2013.01); *C08F 220/06* (2013.01)
USPC ........................................ 424/70.21

(58) Field of Classification Search
None
See application file for complete search history.

(56) References Cited

U.S. PATENT DOCUMENTS

2008/0014154 A1* 1/2008 Mougin et al. .................. 424/59
2008/0292577 A1* 11/2008 Mougin et al. ............. 424/70.17

FOREIGN PATENT DOCUMENTS

| EP | 0372546 A2 | 6/1990 |
|---|---|---|
| EP | 1765893 A2 | 3/2007 |
| EP | 1769011 A2 | 4/2007 |
| FR | 2872514 A1 | 1/2006 |
| JP | 07-285831 A | 10/1995 |
| JP | 2000-302649 A | 10/2000 |
| JP | 2002-284627 A | 10/2002 |
| JP | 2002-322219 A | 11/2002 |
| JP | 2003-055164 A | 2/2003 |
| WO | WO-00/39176 A1 | 7/2000 |

* cited by examiner

*Primary Examiner* — Brian Gulledge
(74) *Attorney, Agent, or Firm* — Novak Druce Connolly Bove + Quigg LLP

(57) ABSTRACT

The present invention relates to novel ethylenic copolymers comprising:
a) from 25 to 95% by weight of monomer of formula (I), comprising PEG units;
b) from 4 to 50% by weight of cationic monomer or one of its salts;
c) from 1 to 35% by weight of anionic monomer and/or its salts.

The invention also relates to cosmetic compositions, in particular hair compositions, comprising said copolymers and to a cosmetic treatment method employing them.

36 Claims, No Drawings

ETHYLENE COPOLYMER WITH PEG, CATIONIC AND ANIONIC UNITS, COSMETIC COMPOSITION INCLUDING SAME AND TREATMENT METHOD

CROSS-REFERENCE TO RELATED APPLICATIONS

This application is a 35 U.S.C. 371 National Stage Application of International Application No. PCT/FR2010/050418, filed Mar. 11, 2010, claiming priority from French Patent Application No. 0952339, filed Apr. 9, 2009, U.S. Provisional Patent Application No. 61/169,003, filed Apr. 14, 2009, French Patent Application No. 0903356, filed Jul. 8, 2009 and French Patent Application No. 0956455, filed Sep. 21, 2009, the entire contents of which are incorporated herein by reference in their entirety.

The present invention relates to novel polymers, to their use, in particular in cosmetics, and to the compositions comprising them.

It is known to employ polymers in the cosmetic field and in particular in the hair field, for example in order to contribute hold or styling of the hair.

Use is made, in the field of "rinse-out" hair compositions, such as shampoos or conditioners, in particular of water-soluble synthetic cationic polymers which are known to contribute a good cosmetic quality to the hair; however, these polymers do not contribute any shaping effect to the hair. It is the same with natural derived cationic polymers, such as modified guar gums, which also contribute a cosmetic nature without making shaping possible. Polymers which contribute styling and an acceptable cosmetic quality are unknown in the field of rinse-out compositions. A constant search is under way, in the field of "leave-in" hair compositions, such as styling products of lacquer, styling gel or styling spray type, for polymers which contribute styling effects and hold to the hair. Known styling products include polymers comprising amine units, such as polymers based on vinylpyrrolidone and on dimethylaminoethyl methacrylate (Gaffix polymers). However, the compositions obtained exhibit an unsatisfactory hold over time. Also known are polymers of Luviquat type, based on quaternized vinylimidazole and on vinylpyrrolidone, which contribute softness but which thicken the compositions.

Provision has also been made for polymers comprising both polyethylene glycol (meth)acrylate (PEGM) units and cationic units.

Thus, EP372546 discloses copolymers based on PEGM and on monomers of ($C_1$-$C_8$ alkyl)(meth)acrylamide type which can comprise cationic monomers. However, these polymers comprise a low proportion of cationic monomers, which does not allow them to generate appropriate cosmetic effects, in particular a deposited layer on the individual hair which is sufficient to contribute the desired properties.

The document JP2002-322219 describes polymers comprising PEGM units in combination with hydrophobic monomers based on polypropylene glycol (PPO) or on polytetramethylene oxide and with cationic monomers. In point of fact, it has been found that these polymers do not make it possible to obtain satisfactory cosmetic properties.

In addition, the patent JP2002-284627 discloses a composition comprising cationic polymers in which the monomers of PEG type are combined with monomers comprising quaternary amine units. In point of fact, the presence of quaternary units can result, as the product is being applied, in an excess deposit layer which can in some cases harm the cosmetic quality of the composition. Furthermore, these polymers comprise a low level of cationic charge which does not make possible optimum affinity for the individual hair. In addition, JP2003-055164 discloses polymers comprising units of PEGM type; however, these polymers are crosslinked, which makes it difficult to control their synthesis.

The document JP2000-302649 also describes a hair composition comprising a polymer which comprises cationic monomers comprising quaternary amines, monomers having a polyether group, in particular of PEG or PPO type, and optional monomers which can be mainly hydrophobic (for example stearyl methacrylate).

In addition, the patent JP07-285831 discloses capillary compositions comprising a polymer which comprises monomers of PEGM type in combination with ionic, cationic or amphoteric monomers and additional monomers of $C_1$-$C_{24}$ alkyl (meth)acrylate type which are mainly hydrophobic.

In these documents, the presence of hydrophobic comonomers, for example of butyl or stearyl acrylate type, does not make it possible to obtain suitable cosmetic properties, in particular does not make it possible to obtain good disentangling of wet hair, immediately after shampooing.

Provision has also been made, for example in the applications EP1769011 and EP1765893, for polymers capable of contributing a styling effect and an acceptable cosmetic quality; these polymers are composed of cationic units in a generally predominant amount and of PEGM units, and can be neutralized. The PEGMs employed can have a low molecular weight.

However, it has been found that the cosmetic properties contributed by these polymers can still be improved; in particular, the cosmetic properties, such as the feel, in particular in a wet environment (on damp or wet hair), and build up (laden hair).

An attempt is under way, in the field of hair care, in particular of the care of sensitized hair, especially which has been subjected to dyeing operations, to contribute cosmetic properties to wet hair, in particular improved feel, and also sheen, softness and disentangling in a dry environment (to dry hair). It is known that hair sensitized, that is to say damaged and/or embrittled, to various degrees by the action of atmospheric agents, in particular light, and also by the repeated action of various mechanical or chemical treatments, such as permanent waves, hair straightening, dyeing and bleaching, may exhibit a detrimental change in the hair fiber, in particular a decline in the mechanical properties, such as the tensile strength, the breaking load and elasticity. The individual hair may be more hydrophilic and may lose a portion of the scales, which is reflected by great difficulty in disentangling and in styling the hair and a loss of softness. It is possible, in order to overcome this, to employ cationic surfactants of the cetyltrimethylammonium type, in oil-in-water emulsion, in the presence of fatty alcohols. However, the cosmetic properties are not optimum and the formulation of these compositions is complicated: compromise between the stability of the emulsion and the nongreasy feel to be found, in particular.

The aim of the present invention is to overcome all of these disadvantages and to provide polymers which, placed in a cosmetic composition, in particular a hair composition, make it possible to contribute improved cosmetic properties, in particular disentangling and feel properties, mainly in a wet environment but also in a dry environment. Furthermore, the use of these polymers makes it possible to avoid problems of build up, that is to say the production of "heavy", excessively laden, hair as the compositions are applied.

A subject matter of the present invention is thus an ethylenic copolymer, or its salts, comprising, as % by weight with respect to the total weight of the polymer:
a) from 25 to 95% by weight of monomers of formula (I), alone or as a mixture, as defined below,
b) from 4 to 50% by weight of cationic monomer or one of its salts, alone or as a mixture, of formula (II) as defined below;
c) from 1 to 35% by weight of anionic monomer and/or its salts, alone or as a mixture, chosen from maleic anhydride or those of formula (III) as defined below.

Another subject matter of the invention is a cosmetic composition comprising said ethylenic copolymer.

It has been found that the polymers according to the invention contribute suitable conditioning effects, in particular softness to the touch and disentangling, to wet hair (in a wet environment) and to dry hair (in a dry environment).

Without being committed to the present explanation, it may be considered that this is due to the presence and to the length of the PEG chain.

By virtue of their cationic nature, they also exhibit an excellent affinity for keratinous substrates, such as the hair, nails and horny layer of the epidermis, on which keratin confers a negative charge.

Finally, by virtue of their anionic nature, they make it possible to avoid problems of build up.

The polymers according to the invention have advantageous cosmetic properties, for example during application in a formulation of shampoo type: the hair easily disentangles during the shampooing and exhibits softness; the compositions according to the invention also make possible, once the hair is dried, particularly advantageous shaping of the hair.

The polymers according to the invention can be conveyed in water, that is to say are soluble or dispersible in water, which makes it possible to employ them in cosmetic compositions, in particular hair compositions, which are generally aqueous-based.

The term "water-soluble" or "soluble in water" is understood to mean that the polymer forms a clear solution in water, in a proportion of at least 5% by weight, at 25° C.

The term "water-dispersible" or "dispersible in water" is understood to mean that the polymer forms, in water, at a concentration of 5% by weight, at 25° C., a stable suspension or dispersion of fine particles, generally spherical particles. The mean size of the particles forming said dispersion is less than 1 μm and more generally varies between 5 and 600 nm, preferably from 10 to 250 nm. These particle sizes are measured by light scattering.

The ethylenic copolymer according to the invention thus comprises at least one monomer of formula (I), which can be present alone or as a mixture:

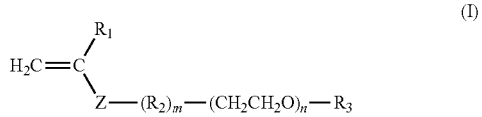

(I)

in which:
R$_1$ is a hydrogen atom or a methyl radical,
Z is a divalent group chosen from —COO—, —CONH—,
R$_2$ is a saturated or unsaturated, optionally aromatic, linear, branched or cyclic, divalent carbon-based radical which comprises from 1 to 18 carbon atoms and which can comprise from 1 to 4 heteroatoms chosen from O, N or S;
m is 0 or 1,
n is an integer between 65 and 700,
R$_3$ is a hydrogen atom or a saturated or unsaturated, optionally aromatic, linear, branched or cyclic, carbon-based radical which comprises from 1 to 30 carbon atoms and which can comprise from 1 to 4 heteroatoms chosen from O, N or S.

In the R$_2$ radical, the heteroatom or heteroatoms, when they are present, can be inserted in the chain of said R$_2$ radical or else said R$_2$ radical can be substituted by one or more groups comprising them, such as OH, SH or amino (NR'R", with R' and R", which are identical or different, representing a hydrogen or a linear or branched C$_1$-C$_4$ alkyl, in particular methyl or ethyl).

In particular, R$_2$ can be:
a C$_1$-C$_{18}$ alkylene radical, such as methylene, ethylene, propylene, n-butylene, isobutylene, tert-butylene, n-hexylene, n-octylene, n-dodecylene, n-octadecylene, n-tetradecylene or n-docosanylene; optionally substituted by OH or NR'R";
a phenylene radical —C$_6$H$_4$-(ortho, meta or para), optionally substituted by a C$_1$-C$_{12}$ alkyl;
a benzylene radical —C$_6$H$_4$—CH$_2$—, optionally substituted by a C$_1$-C$_{10}$ alkyl;
a linear or branched divalent C$_1$-C$_{12}$ alkyleneoxy radical, for example a —CH$_2$—CH$_2$—CH$_2$—O— (propyloxy) radical.

Preferably, R$_2$ is a linear C$_1$-C$_6$ alkylene radical.
Preferably, n is between 75 and 500, better still between 80 and 400, indeed even between 90 and 300, preferably between 95 and 250 and even better still between 100 and 200.

Preferably, R$_3$ is a hydrogen atom; a benzyl radical; a phenyl radical optionally substituted by a C$_1$-C$_{12}$ alkyl; or a C$_1$-C$_{30}$, in particular C$_1$-C$_{22}$, indeed even C$_2$-C$_{16}$, alkyl radical optionally comprising from 1 to 4 heteroatoms chosen from O, N and S. Mention may be made of the methyl, ethyl, propyl, benzyl, ethylhexyl, lauryl, stearyl and behenyl radicals.

Mention may be made, among the preferred monomers of formula (I), of:
poly(ethylene glycol)(meth)acrylate, in which R$_1$ is H or methyl; Z is COO, m=0 and R$_3$=H;
methyl poly(ethylene glycol)(meth)acrylate, also known as methoxypoly-(ethylene glycol)(meth)acrylate, in which R$_1$ is H or methyl, Z is COO, m=0 and R$_3$=methyl;
alkyl poly(ethylene glycol)(meth)acrylates, in which R$_1$ is H or methyl, Z is COO, m=0 and R$_3$=alkyl;
phenyl poly(ethylene glycol)(meth)acrylates, also known as poly(ethylene glycol) phenyl ether (meth)acrylates, in which R$_1$ is H or methyl, Z is COO, m=0 and R$_3$=phenyl.

The monomers of formula (I) which are very particularly preferred are chosen from poly(ethylene glycol)(meth)acrylates and methyl poly(ethylene glycol) (meth)acrylates, preferably those having a molecular weight of between 2800 and 30 000 g/mol, in particular between 3500 and 20 000 g/mol, and even between 4000 and 10 000 g/mol.

Examples of commercial monomers are:
the polyethylene glycol 8000 or 4000 methacrylates from Monomer & Polymer Dajac Laboratories;
the methacryles of PEG with an MW of 5000 from Arkema, having the trade name Norsocryl N-405;
the methacrylates of methoxypoly(ethylene glycol) with an MW of 5000, available from Evonik under the trade name MPEG-5000-MA;
the methoxypoly(ethylene glycol) methacrylates 5K, 10K, 12K, 20K and 30K from Sunbio.

The monomer of formula (I), alone or as a mixture, is present in a proportion of 25 to 95% by weight, with respect to the weight of the final polymer, in particular in a proportion of 30 to 90% by weight, preferably of 32 to 85% by weight, indeed even of 35 to 70% by weight.

The ethylenic copolymer according to the invention also comprises at least one cationic monomer or one of its salts, which can be present alone or as a mixture, of formula (II):

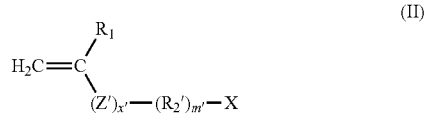
(II)

in which:
R₁ is a hydrogen atom or a methyl radical,
Z' is a divalent group chosen from —COO—, —C(O)— and —CONH—,
x' is 0 or 1,
R₂' is a saturated or unsaturated, optionally aromatic, linear, branched or cyclic, divalent carbon-based radical of from 1 to 18 carbon atoms which can comprise from 1 to 4 heteroatoms chosen from O, N or S,
m' is 0 or 1;
X is chosen from:
(a) a group of formula —N(R₆)(R₇) with R₆ and R₇ representing, independently of one another, either (i) a hydrogen atom, or (ii) a saturated or unsaturated, optionally aromatic, linear, branched or cyclic, alkyl group comprising from 1 to 12 carbon atoms, or (iii) R₆ and R₇ form, with the nitrogen atom, a saturated or unsaturated, optionally aromatic, ring comprising 5, 6 or 7 ring members chosen from CH, CH₂, O, N, NH, S or C(O); or else
(b) X represents an —R₆'—N—R₇'— group, in which R₆' and R₇' form, with the nitrogen atom, a saturated or unsaturated, optionally aromatic, ring comprising 5, 6 or 7 ring members chosen from CH, CH₂, O, N, NH, S or C(O).

The term "cationic monomer" is understood to mean a monomer comprising units capable of having a cationic charge in the pH range between 3 and 12. These units do not have a permanent charge, whatever the pH. The cationic unit does not have to be protonated at each of these pH values.

In the R₂' radical, the heteroatom or heteroatoms, when they are present, can be inserted in the chain of said R₂' radical or else said R₂' radical can be substituted by one or more groups comprising them, such as OH, SH or NR'R" (with R' and R", which are identical or different, representing a hydrogen or a linear or branched C₁-C₄ alkyl, in particular methyl or ethyl).

In particular, R₂' can be:
a C₁-C₁₈ alkylene radical, such as methylene, ethylene, propylene, n-butylene, isobutylene, tert-butylene, n-hexylene, n-octylene, n-dodecylene, n-octadecylene, n-tetradecylene or n-docosanylene; optionally substituted by OH or NR'R";
a phenylene radical —C₆H₄-(ortho, meta or para), optionally substituted by a C₁-C₁₂ alkyl;
a benzylene radical —C₆H₄—CH₂—, optionally substituted by a C₁-C₁₀ alkyl;
a linear or branched divalent C₁-C₁₂ alkyleneoxy radical, in particular a propyloxy —CH₂CH₂CH₂O— radical.
Preferably, R₂' is a linear C₁-C₆ alkylene phenylene or benzylene radical.

Preferably, R₆ and R₇ can be chosen, independently of one another, from hydrogen or a linear C₁-C₁₈ alkyl radical and in particular methyl, ethyl, propyl, isopropyl, n-butyl, tert-butyl, isobutyl, octyl, lauryl or stearyl, Preferably, R₆ and R₇ are chosen, independently of one another, from H, CH₃ and C₂H₅.

In particular, X can be an —NH₂, —N(CH₃)₂ or —N(C₂H₅)₂ radical.

When R₆ and R₇ form a ring with the nitrogen atom, this ring is preferably a 5- or 6-membered ring, including the nitrogen atom, and can comprise another heteroatom as ring member. In particular, X can be a radical as follows:

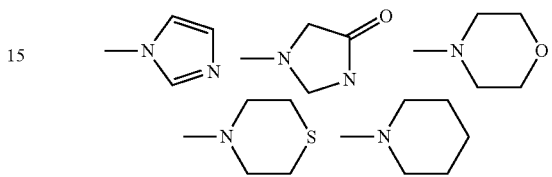

When X represents an —R₆'—N—R₇'— group, this ring preferably comprises 6 ring members, including the nitrogen atom, and can comprise another heteroatom as ring member. In particular, X can be a radical as follows:

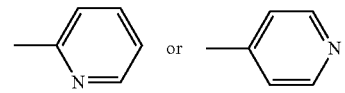

Mention may be made, among the preferred monomers of formula (II), and their salts, of:

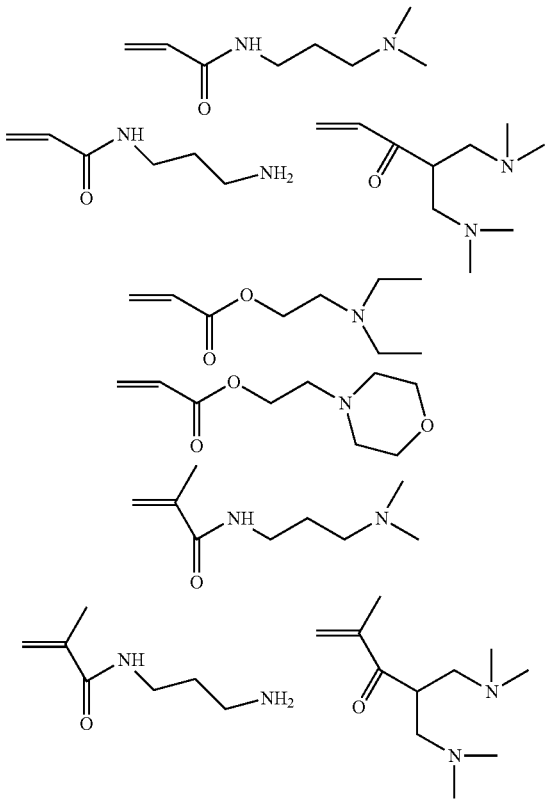

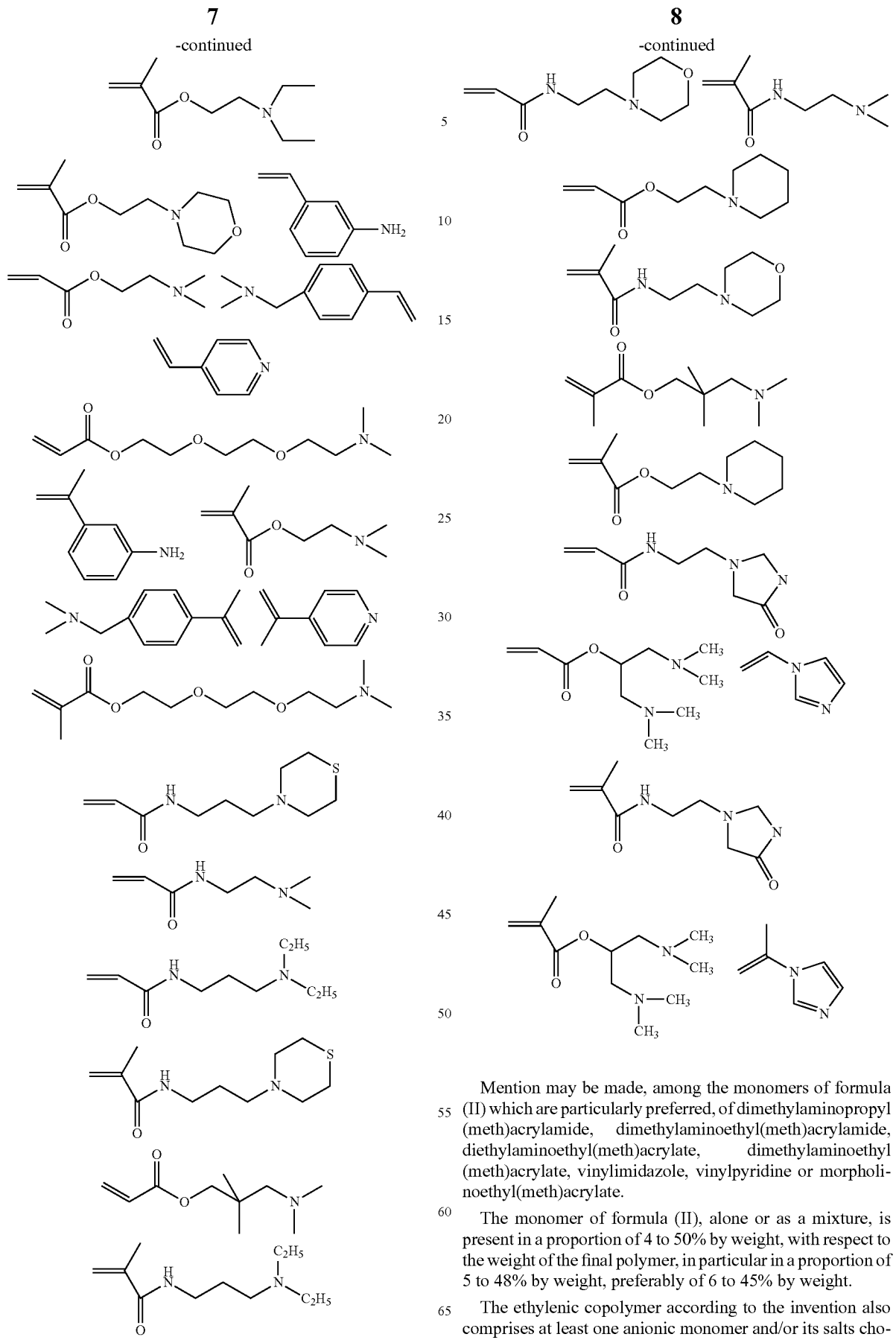

Mention may be made, among the monomers of formula (II) which are particularly preferred, of dimethylaminopropyl (meth)acrylamide, dimethylaminoethyl(meth)acrylamide, diethylaminoethyl(meth)acrylate, dimethylaminoethyl (meth)acrylate, vinylimidazole, vinylpyridine or morpholinoethyl(meth)acrylate.

The monomer of formula (II), alone or as a mixture, is present in a proportion of 4 to 50% by weight, with respect to the weight of the final polymer, in particular in a proportion of 5 to 48% by weight, preferably of 6 to 45% by weight.

The ethylenic copolymer according to the invention also comprises at least one anionic monomer and/or its salts chosen from maleic anhydride and/or those of formula (III):

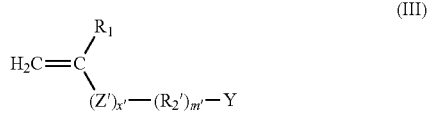

in which:
- $R_1$, $Z'$, $x'$, $R_2'$ and $m'$ have the same meanings as those given above for the formula (II);
- Y is a group chosen from —COOH, —SO$_3$H, —OSO$_3$H, —PO$_3$H$_2$ and —OPO$_3$H$_2$.

It is understood that, according to the state of the art, the SO$_4$H$_2$ and PO$_4$H$_2$ groups are bonded to $R_2'$ via the oxygen atom, whereas the SO$_3$H and PO$_3$H groups are bonded to $R_2'$ via the S and P atoms respectively.

Mention may be made, among the preferred anionic monomers, of maleic anhydride, acrylic acid, methacrylic acid, crotonic acid, itaconic acid, fumaric acid, maleic acid, 2-carboxyethyl acrylate (CH$_2$=CH—C(O)—O—(CH$_2$)$_2$—COOH), styrenesulfonic acid, 2-acrylamido-2-methylpropanesulfonic acid, vinylbenzoic acid, vinylphosphonic acid, sulfopropyl(meth)acrylate and the salts of these.

The monomer of formula (III), alone or as a mixture, is present in a proportion of 1 to 35% by weight, with respect to the weight of the final polymer, in particular in a proportion of 1.5 to 32% by weight, preferably of 2 to 30% by weight.

In a preferred embodiment, the ethylene copolymer according to the invention is essentially composed of monomer(s) of formula (I), of formula (II) and of formula (III), which means that it does not comprise, optionally, other monomers than those mentioned above.

The copolymers according to the invention are non-crosslinked. They are provided in the form of random ethylenic copolymers, generally film-forming copolymers, of one or more ethylenic monomers comprising PEG groups (the PEG groups being pendant groups along the backbone), of one or more ethylenic monomers comprising cationic functional groups (neutralized and nonquaternary amines) and of one or more ethylenic monomers comprising anionic functional groups.

The term "film-forming" polymer is understood to mean a polymer capable of forming, by itself alone or in the presence of an additional agent which is able to form a film, a continuous and adherent film on a support, in particular on keratinous substances.

It is possible to neutralize one and/or other of the monomers constituting the copolymer before polymerization, or else to neutralize the copolymer once formed. Preferably, the copolymer is neutralized after it has been formed.

Preferably, the amine units are neutralized; the neutralizing of the acid units is optional.

Preferably, the copolymer is neutralized until a pH of less than or equal to 7.5 is obtained, for a 5% aqueous solution of said polymer.

The neutralizing of the amine units, belonging to the polymer and/or to the monomers, can be carried out by a Bronsted acid or a mixture of such acids; in particular by an inorganic acid, such as sulfuric acid, hydrochloric acid, hydrobromic acid, hydriodic acid, phosphoric acid or boric acid; or by an organic acid, which can comprise one or more carboxylic acid, sulfonic acid or phosphonic acid groups. It can be linear, branched or cyclic aliphatic acids or also unsaturated or aromatic acids. These acids can additionally comprise one or more heteroatoms chosen from O or N, for example in the form of hydroxyl groups. Mention may in particular be made of acetic acid, terephthalic acid, HOOC-PEG-COOH acid, citric acid, tartaric acid, the betaine HCl or betaine hydrochloride of formula (CH$_3$)$_3$N$^+$CH$_2$CO$_2$H Cl$^-$; gluconic acid or 2-ethylcaproic acid. Preferably, betaine hydrochloride is used.

The acid groups can be partially or completely neutralized by an inorganic base, such as LiOH, NaOH, KOH, Ca(OH)$_2$, NH$_4$OH, Mg(OH)$_2$ or Zn(OH)$_2$, or by an organic base, such as a primary, secondary or tertiary alkylamine, which can comprise one or more nitrogen and/or oxygen atoms, for example one or more alcohol functional groups. Mention may in particular be made of triethanolamine, 2-amino-2-methylpropanol, triethylamine or butylamine.

The polymers according to the invention can be prepared according to the standard methods for conventional radical polymerization well known to a person skilled in the art.

In particular, these polymers can be prepared by:
- direct polymerization in solution in water, with or without preneutralization of the cationic and/or anionic unit;
- polymerization in emulsion in water, with or without preneutralization of the cationic and/or anionic unit and with use of a surfactant;
- polymerization in an organic solvent, such as ethanol or methyl ethyl ketone, with or without preneutralization of the cationic and/or anionic unit, followed by a stage of dissolution or dispersion in water with evaporation of the solvent.

These polymerizations can be carried out in the presence of a radical initiator, in particular of peroxide type (Trigonox 21S: tert-butyl peroxy-2-ethylhexanoate) or azo type (AIBN V50: 2,2'-azobis(2-amidinopropane)dihydrochloride), which can be present in a proportion of 0.3 to 5% by weight, with respect to the total weight of monomers.

The copolymers according to the invention exhibit a weight-average molecular weight (Mw) which is preferably between 5000 and 1 000 000 g/mol, in particular between 7000 and 750 000 g/mol, preferably between 10 000 and 500 000 g/mol. The weight-average molar masses (Mw) are determined by gel permeation chromatography or by light scattering, depending on the accessibility of the method (solubility of the polymers under consideration).

The polymers according to the invention can preferably be conveyed in an aqueous medium, that is to say that they are preferably water-soluble or water-dispersible.

Dissolving or dispersing in water can be carried out by direct dissolution of the polymer, if it is soluble, or else by neutralization of the amine and/or acid units, such as to render the polymer soluble or dispersible in water.

Dissolving or dispersing in water can also be carried out via an intermediate stage of dissolution in an organic solvent, followed by addition of water, before evaporation of the organic solvent.

The polymers according to the invention have a very particular application in the field of cosmetics. They can be present in the composition in the dissolved form, for example in the form dissolved in water or an organic solvent, or else in the form of an aqueous or organic dispersion.

They can be used in cosmetic compositions in a proportion of 0.1 to 20% by weight of dry matter, in particular of 0.5 to 15% by weight, indeed even of 1 to 10% by weight, better still of 2 to 8% by weight, with respect to the total weight of the composition.

The cosmetic compositions according to the invention comprise, in addition to said polymers, a cosmetically acceptable medium, that is to say a medium compatible with keratinous substances, such as the skin of the face or of the body, the hair, the eyelashes, the eyebrows and the nails.

Preferably, the cosmetically acceptable medium comprises a solvent or dispersing medium for the polymers according to the invention which can comprise at least one compound chosen from water, alcohols, polyols, esters, carbon-based oils, silicone oils, fluorosilicone oils and their mixtures.

Preferably, the cosmetically acceptable medium can comprise water or a mixture of water and of hydrophilic organic solvent(s), such as alcohols and in particular linear or branched $C_1$-$C_6$ monoalcohols, such as ethanol, tert-butanol, n-butanol, isopropanol or n-propanol, or 2-butoxyethanol; and polyols, such as glycerol, diglycerol, ethylene glycol, propylene glycol, sorbitol, pentylene glycol and polyethylene glycols; or else polyol or glycol ethers, in particular $C_2$ ethers, such as diethylene glycol monoethyl ether and monomethyl ether; and hydrophilic $C_2$-$C_4$ aldehydes.

The composition according to the invention can additionally comprise at least one cosmetically acceptable adjuvant conventionally used in cosmetic compositions, in particular intended to be applied to keratinous fibers.

Mention may in particular be made, as cosmetically acceptable adjuvant, of gelling agents, thickeners; associative or nonassociative polymers; anionic, nonionic, cationic and/or amphoteric surfactants; propenetrating agents, emulsifiers, fragrances, preservatives, pigments, dyes, fillers, sunscreens; coloring materials, proteins, vitamins, provitamins; fixing or nonfixing polymers; moisturizing agents, emollients, softening agents; mineral, vegetable or synthetic oils; hydrophilic or lipophilic active principles, ceramides, pseudoceramides; antifoaming agents, antiperspirants, agents for combating free radicals, bactericidal agents, antidandruff agents, agents for combating hair loss, pearlescence agents and their mixtures. A person skilled in the art will take care to choose these optional adjuvants and their amounts so that the advantageous properties of the composition according to the invention are not, or not substantially, detrimentally affected by the envisaged addition.

The compositions according to the invention can be provided in all the formulation forms conventionally used for a topical application and in particular in the form of an aqueous, alcoholic or aqueous/alcoholic solution or suspension, of an oily solution or suspension, of a solution or dispersion of the lotion or serum type, of an oil-in-water, water-in-oil or multiple emulsion; of an aqueous or anhydrous gel, of a dispersion of vesicles, in particular lipid vesicles; of a two-phase or multiphase lotion; of a spray; this composition can have the appearance of a thickened or nonthickened lotion, of a thickened or nonthickened cream, of an aqueous or anhydrous gel, of a foam, of a milk, of a serum, of an ointment, of a soft paste, of a salve, of a cast or molded solid, in particular in the form of a stick or in a dish, or of a compacted solid. It can optionally be packaged in a pump-action spray or in an aerosol container.

A person skilled in the art can choose the appropriate formulation form and its method of preparation on the basis of his general knowledge, taking into account, on the one hand, the nature of the constituents used, in particular their solubility in the vehicle, and, on the other hand, the application envisaged for the composition.

The cosmetic composition of the invention can be provided in the form of a product for caring for, cleaning and/or making up the skin of the body or of the face, the lips, the eyelashes, the nails and the hair, of an antisun or self-tanning product, of a body hygiene product or of a hair product, in particular for caring for, cleaning, styling or dyeing the hair.

It has in particular a particularly advantageous application in the hair field, in particular for the form retention of the hairstyle, the shaping of the hair and the cleaning of the hair.

The hair compositions are preferably shampoos, conditioners, styling or care gels, care lotions or creams, hairsetting lotions, blow-drying lotions, or fixing and styling compositions, such as lacquers or sprays. The lotions can be packaged in various forms, in particular in vaporizers, pump-action sprays or aerosol containers, in order to provide for application of the composition in the vaporized form or in the foam form.

It can also be provided in the form of a hair dyeing composition; of a perming, hair straightening or bleaching composition; or of a leave-in composition, to be applied before or after a dyeing, a bleaching, a perming or a hair straightening or between the two stages of a perming or of a hair straightening.

It can also be provided in the form of a composition for caring for the skin, lips and/or superficial body growths, or in the form of a composition for cleaning the skin, for example a make-up-removing product or a bath or shower gel. It can also be provided in the form of a color-free care product intended to treat the skin and in particular to moisturize it, to smooth it, to depigment it, to nourish it, to protect it from solar radiation or to confer a specific treatment thereon.

It can also be provided in the form of a body hygiene composition, in particular in the form of a deodorant or antiperspirant product or in the form of a depilatory composition.

It can also be provided in the form of a product, in particular a colored product, for making up the skin of the body or of the face, or the hair, in particular a foundation, optionally exhibiting care properties, a blusher, a face powder, an eye shadow, a concealer or an eyeliner; a product for making up the lips, such as a lipstick, optionally exhibiting care properties, a lip gloss or lip pencil; a product for making up the superficial body growths, such as the nails, the eyelashes, in particular in the form of a cake mascara, the eyebrows and hair; or a product for the temporary tatooing of the skin of the body.

Advantageously, the composition according to the invention is a hair composition for conditioning the hair and can be provided in the form of a lotion, cream, gel, foam or spray.

Another subject matter of the invention is a method for the cosmetic treatment, in particular for the making up, caring for, cleaning, dyeing or shaping, of keratinous substances, in particular of the skin of the body or of the face, the nails, the hair, the eyelashes or the lips, comprising the application to said substances of a cosmetic composition as defined above.

Preferably, it is a cosmetic treatment method for reshaping and/or the form retention of the hair, comprising the application to said hair of a composition according to the invention, optionally followed by a rinsing stage.

The invention is illustrated in more detail in the following examples.

EXAMPLE 1

Synthesis of Polymers According to the Invention 20 g of methyl ethyl ketone (MEK), 4.5 g of dimethylaminopropylmethacrylamide (DMAPMA), 4.5 g of Norsocryl N-405 polymer from Arkema (96% by weight of MW=5000 polyethylene glycol methacrylate+4% by weight of methacrylic acid) and 1 g of acrylic acid are introduced into a 50 ml reactor which is under temperature control and which is equipped with an orbital stirrer, and the mixture is heated at reflux for 30 minutes. 0.1 g of initiator (Trigonox 21S) is then added and reflux is then continued; after 2 hours, 0.05 g of initiator is again added; reflux is continued for a further 2 hours and 0.05 g of initiator is again added. The mixture is left to heat at reflux for a total of 7 hours. The reaction is monitored by NMR.

The reaction medium is 100% neutralized by addition of 4.5 g of betaine hydrochloride in 30 ml of water; the solvent (MEK) is subsequently evaporated on a rotary evaporator.

A PEGM(5000)-co-DMAPMA-co-acrylic acid-co-methacrylic acid copolymer, in proportions of 43.2/45/10/1.8, is obtained in solution in water, with a solids content of 30%.

Polymers 2 to 6 below are prepared in an identical way by varying the amounts of starting monomers (% by weight).

|  | % Norsocryl N-405 (% PEGM 5000 + % methacrylic acid) | % DMAPMA | % acrylic acid | Solids content (%) |
|---|---|---|---|---|
| Polymer 1 | 45 (43.2 + 1.8) | 45 | 10 | 30 |
| Polymer 2 | 35 (33.6 + 1.4) | 35 | 30 | 24 |
| Polymer 3 | 70 (67.2 + 2.8) | 20 | 10 | 26 |
| Polymer 4 | 68.2 (65.5 + 2.7) | 13.6 | 18.2 | 21 |
| Polymer 5 | 75 (72 + 3) | 25 | 0 | 35 |
| Polymer 6 | 50 (48 + 2) | 50 | 0 | 36 |

Test

The slippery nature of the polymers is evaluated by using a tribometer of pin-on-disk type, 3% by weight solutions of the above polymers in water are prepared and then the solution is deposited on a moving substrate which is brought into contact with a ball.

The frictional force between the ball and the moving substrate is then measured. The smaller the frictional force between the two surfaces, the greater the slippery nature of the polymer. The frictional force is expressed in newtons (N).

The following results are obtained:

| Frictional force on a hydrophobic substrate (N) | |
|---|---|
| Polymer 2 | 0.28 |
| Polymer 3 | 0.25 |
| Polymer 5 | 0.35 |
| Polymer 6 | 0.35 |

It is found that the polymers according to the invention exhibit a certain slippery nature.

EXAMPLE 2

Cosmetic Composition

A cosmetic composition is prepared which comprises (% by weight)

| Polymer 2 according to example 1 | 1% (DM: dry matter) |
|---|---|
| Preservative | q.s. |
| Water | q.s.p for 100% |

5 ml of this composition are applied to hair (locks of 2.5 g). Very good disentangling is found in a wet environment and a soft feel is found in a dry environment.

EXAMPLE 3

Synthesis of a Polymer According to the Invention 300 ml of water and 9 g of betaine hydrochloride are introduced into a 2 liter reactor. The reaction medium is heated to 90° C. and then the two following preparations are run in simultaneously over 30 minutes: the first comprises 10 g of dimethylaminopropylmethacrylamide (DMAPMA) and 0.75 g of Trigonox 21S; the second comprises 87.3 g of PEGM(5000), 2.7 g of methacrylic acid and 93 ml of water. After heating for 7 hours, a further 150 ml of water are added to the reaction medium and then it is concentrated under reduced pressure at 50° C. in order to obtain 465 g of a fluid and transparent solution comprising 22.6% of polymer.

The polymer exhibits a composition of 87.3% of PEGM (5000), 2.7% of methacrylic acid and 10% of DMAPMA (% by weight).

EXAMPLE 4

Synthesis of a Polymer According to the Invention 300 ml of water and 18 g of betaine hydrochloride are introduced into a 2 liter reactor. The reaction medium is heated to 90° C. and then the following two preparations are run in simultaneously over 30 minutes: the first comprises 20 g of dimethylaminopropylmethacrylamide (DMAPMA) and 0.75 g of Trigonox 21S; the second comprises 77.8 g of PEGM(5000), 2.2 g of methacrylic acid and 82 ml of water. After heating for 7 hours, a further 150 ml of water are added to the reaction medium and then it is concentrated under reduced pressure at 50° C. in order to obtain 433 g of a fluid and transparent solution comprising 23.1% of polymer.

The polymer exhibits a composition of 77.8% of PEGM (5000), 2.2% of methacrylic acid and 20% of DMAPMA (% by weight).

EXAMPLE 5

Synthesis of a Polymer According to the Invention 300 ml of water and 13.5 g of betaine hydrochloride are introduced into a 2 liter reactor. The reaction medium is heated to 90° C. and then the following two preparations are run in simultaneously over 30 minutes: the first comprises 15 g of dimethylaminopropylmethacrylamide (DMAPMA) and 0.75 g of Trigonox 21S; the second comprises 83 g of PEGM (5000), 2 g of methacrylic acid and 88 ml of water. After heating for 7 hours, a further 150 ml of water are added to the reaction medium and then it is concentrated under reduced pressure at 50° C. in order to obtain 470 g of a fluid and transparent solution comprising 21.3% of polymer.

The polymer exhibits a composition of 83% of PEGM (5000), 2% of methacrylic acid and 15% of DMAPMA (% by weight).

The invention claimed is:

1. An ethylenic copolymer or its salts comprising, as % by weight with respect to the total weight of the polymer:

a) from 65.5 to 95% by weight of monomer of formula (I), alone or as a mixture:

15

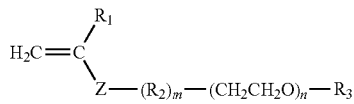
(I)

in which:
R$_1$ is a hydrogen atom or a methyl radical,
Z is a divalent group chosen from —COO—, —CONH—,
R$_2$ is a saturated or unsaturated, optionally aromatic, linear, branched or cyclic, divalent carbon-based radical which comprises from 1 to 18 carbon atoms and which can comprise from 1 to 4 heteroatoms chosen from O, N or S;
m is 0 or 1,
n is an integer between 65 and 700,
R$_3$ is a hydrogen atom or a saturated or unsaturated, optionally aromatic, linear, branched or cyclic, carbon-based radical which comprises from 1 to 30 carbon atoms and which can comprise from 1 to 4 heteroatoms chosen from O, N or S;
b) from 4 to 33.5% by weight of cationic monomer or one of its salts, alone or as a mixture, of formula (II):

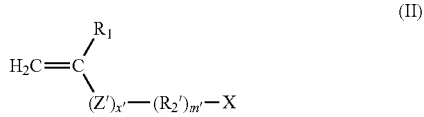
(II)

in which:
R$_1$ is a hydrogen atom or a methyl radical,
Z' is a divalent group chosen from —COO—, —C(O)— and —CONH—,
x' is 0 or 1,
R$_2$' is a saturated or unsaturated, optionally aromatic, linear, branched or cyclic, divalent carbon-based radical of from 1 to 18 carbon atoms which can comprise from 1 to 4 heteroatoms chosen from O, N or S,
m' is 0 or 1;
X is chosen from:
(a) a group of formula —N(R$_6$)(R$_7$) with R$_6$ and R$_7$ representing, independently of one another, either (i) a hydrogen atom, or (ii) a saturated or unsaturated, optionally aromatic, linear, branched or cyclic, alkyl group comprising from 1 to 12 carbon atoms, or (iii) R$_6$ and R$_7$ form, with the nitrogen atom, a saturated or unsaturated, optionally aromatic, ring comprising 5, 6 or 7 ring members chosen from CH, CH$_2$, O, N, NH, S or C(O); or else
(b) X represents an —R$_6$'—N—R$_7$'— group, in which R$_6$' and R$_7$' form, with the nitrogen atom, a saturated or unsaturated, optionally aromatic, ring comprising 5, 6 or 7 ring members chosen from CH, CF$_2$, O, N, NH, S or C(O);
c) from 1 to 30% by weight of anionic monomer and/or its salts, alone or as a mixture, chosen from maleic anhydride and those of formula (III):

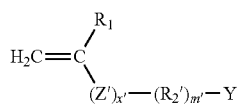
(III)

16 in which:
R$_1$, Z', x', R$_2$' and m' have the meanings given above for the formula (II); and
Y is a group chosen from —COOH, —SO$_3$H, —OSO$_3$H, —PO$_3$H$_2$ and —OPO$_3$H$_2$.

2. The copolymer as claimed in claim 1, in which, in the formula (I), n is between 75 and 500.

3. The copolymer as claimed in claim 1, wherein the monomers of formula (I) are chosen from:
poly(ethylene glycol)(meth)acrylate, in which R$_1$ is H or methyl: Z is COO, m=0 and R$_3$=H;
methyl poly(ethylene glycol)(meth)acrylate, in which R$_1$ is H or methyl, Z is COO, m=0 and R$_3$=methyl;
alkyl poly(ethylene glycol)(meth)acrylates, in which R$_1$ is H or methyl, Z is COO, m=0 and R$_3$=alkyl;
phenyl poly(ethylene glycol)(meth)acrylates, in which R$_1$ is H or methyl, Z is COO, m=0 and R$_3$=phenyl.

4. The copolymer as claimed in claim 1, wherein the monomer of formula (I), alone or as a mixture, is present in a proportion of 70 to 95% by weight with respect to the weight of the final copolymer.

5. The copolymer as claimed in claim 1, wherein the monomer of formula (II) is chosen from, alone or as a mixture, the following monomers and their salts:

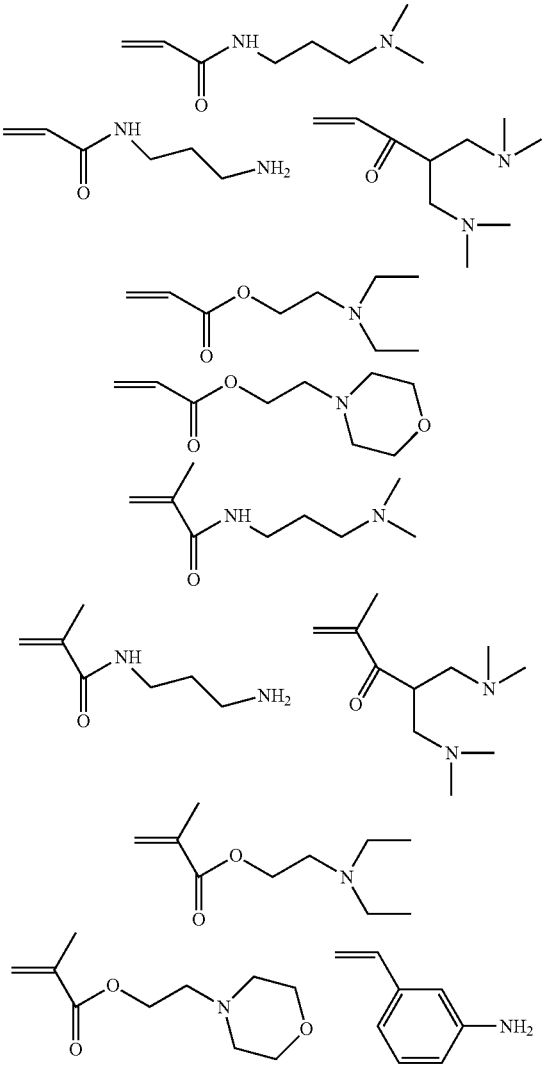

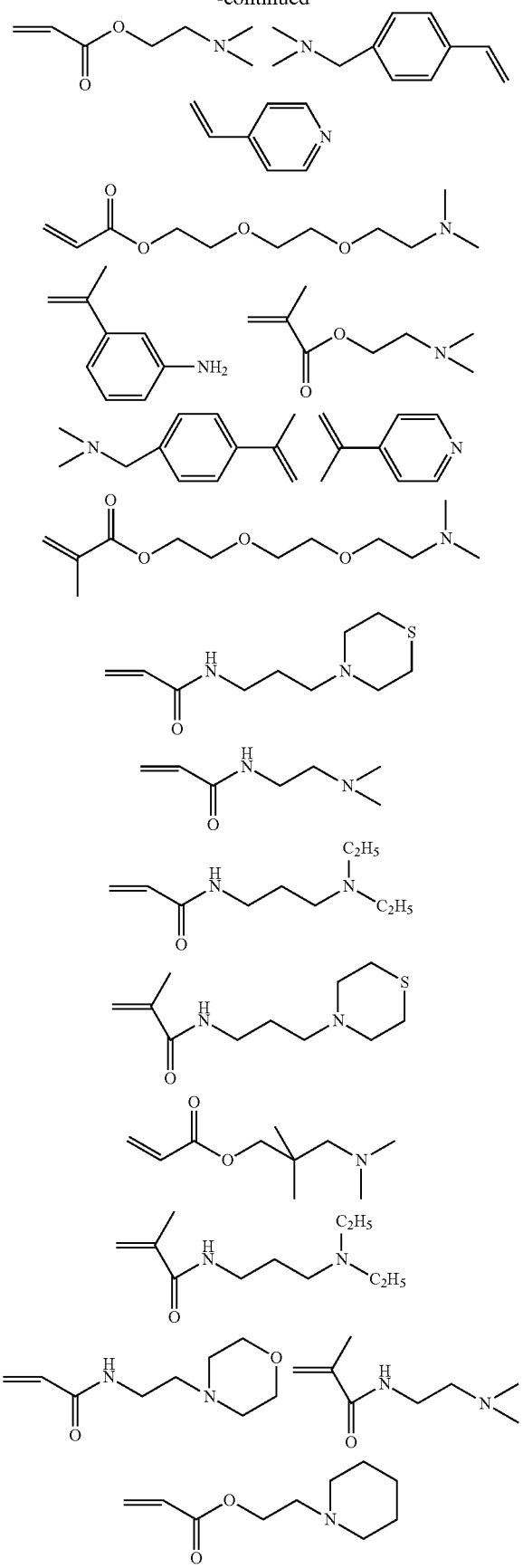

and also dimethylaminopropyl(meth)acrylamide, dimethylaminoethyl(meth)acrylamide, diethylaminoethyl(meth)acrylate, dimethylaminoethyl(meth)acrylate, vinylimidazole, vinylpyridine or morpholinoethyl(meth)acrylate.

6. The copolymer as claimed in claim 1, wherein the monomer of formula (II), alone or as a mixture, is present in a proportion of at least 5% by weight, with respect to the weight of the final copolymer.

7. The copolymer as claimed in claim 1, wherein the anionic monomer is chosen from, alone or as a mixture, maleic anhydride, acrylic acid, methacrylic acid, crotonic acid, itaconic acid, fumaric acid, maleic acid, 2-carboxyethyl acrylate, styrenesulfonic acid, 2-acrylamido-2-methylpropanesulfonic acid, vinylbenzoic acid, vinylphosphonic acid, sulfopropyl(meth)acrylate and the salts thereof.

8. The copolymer as claimed in claim 1, wherein the monomer of formula (III), alone or as a mixture, is present in a proportion of 1.5 to 30% by weight, with respect to the weight of the final copolymer.

9. The copolymer as claimed in claim 1, wherein the copolymer is neutralized by a Bronsted acid or a mixture of such acids.

10. A cosmetic composition, comprising, in a cosmetically acceptable medium, at least one copolymer as defined in claim 1.

11. The composition as claimed in claim 10, wherein the copolymer is present in the form dissolved in water or an organic solvent, or else in the form of an aqueous or organic dispersion.

12. The composition as claimed in claim 10, wherein the copolymer is present, alone or as a mixture, in a proportion of 0.1 to 20% by weight of dry matter with respect to the total weight of the composition.

13. The composition as claimed in claim 10, wherein the cosmetically acceptable medium comprises at least one compound chosen from water, alcohols, polyols, polyol ethers, esters, carbon-based oils, silicone oils, fluorosilicone oils, gelling agents, thickeners; associative or nonassociative polymers; anionic, nonionic, cationic and/or amphoteric surfactants; propenetrating agents, emulsifiers, fragrances, preservatives, pigments, dyes, fillers, sunscreens; coloring materials, proteins, vitamins, provitamins; fixing or nonfixing polymers; moisturizing agents, emollients, softening agents; mineral, vegetable or synthetic oils; hydrophilic or lipophilic active principles, ceramides, pseudoceramides; antifoaming agents, antiperspirants, agents for combating free radicals, bactericidal agents, antidandruff agents, agents for combating hair loss, pearlescence agents and their mixtures.

14. The composition as claimed in claim 10, which is provided in the form of a product for caring for, cleaning and/or making up the skin of the body or of the face, the lips, the eyelashes, the nails and the hair, of an antisun or self-tanning product, of a body hygiene product or of a hair product.

15. The composition as claimed in claim 10, which is provided in the form of a hair composition for conditioning the hair.

16. The copolymer as claimed in claim 2, wherein the monomers of formula (I) are chosen from:
 poly(ethylene glycol)(meth)acrylate, in which $R_1$ is H or methyl; Z is COO, m=0 and $R_3$=H;
 methyl poly(ethylene glycol)(meth)acrylate, in which $R_1$ is H or methyl, Z is COO, m=0 and $R_3$=methyl;
 alkyl poly(ethylene glycol)(meth)acrylates, in which $R_1$ is H or methyl, Z is COO, m=0 and $R_3$=alkyl;
 phenyl poly(ethylene glycol)(meth)acrylates, in which $R_1$ is H or methyl, Z is COO, m=0 and $R_3$=phenyl.

17. The copolymer as claimed in claim 2, wherein the monomer of formula (I), alone or as a mixture, is present in a proportion of 70 to 95% by weight with respect to the weight of the final copolymer.

18. The copolymer as claimed in claim 3, wherein the monomer of formula (I), alone or as a mixture, is present in a proportion of 70 to 95% by weight with respect to the weight of the final copolymer.

19. The copolymer as claimed in claim 2, wherein the monomer of formula (II) is chosen from, alone or as a mixture, the following monomers and their salts:

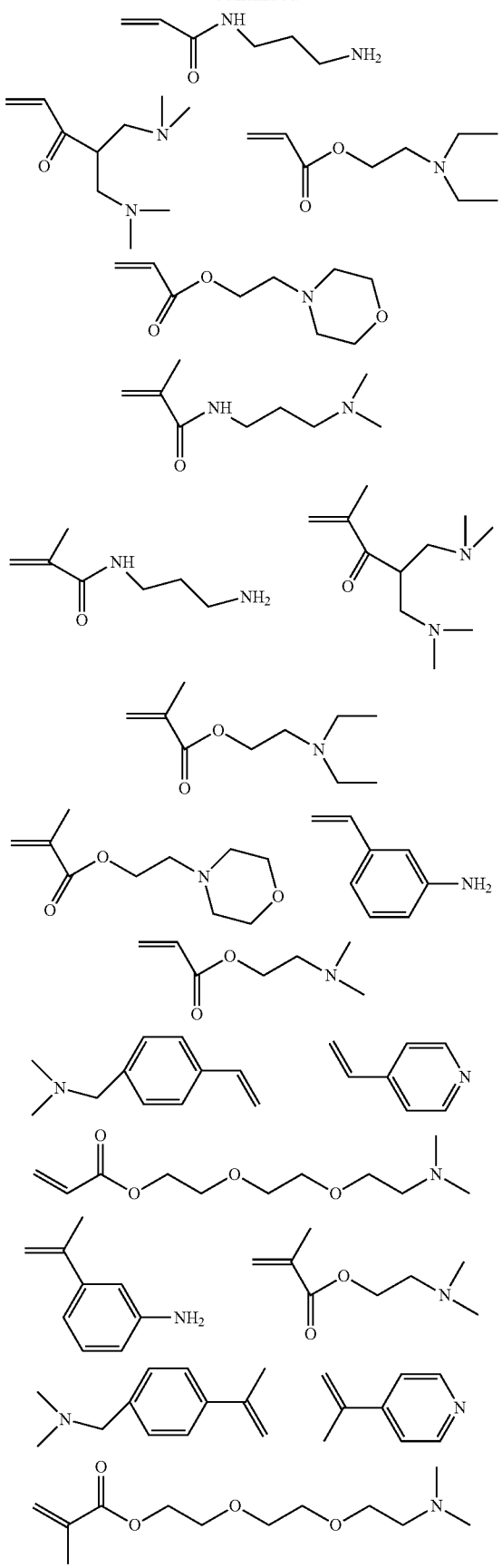

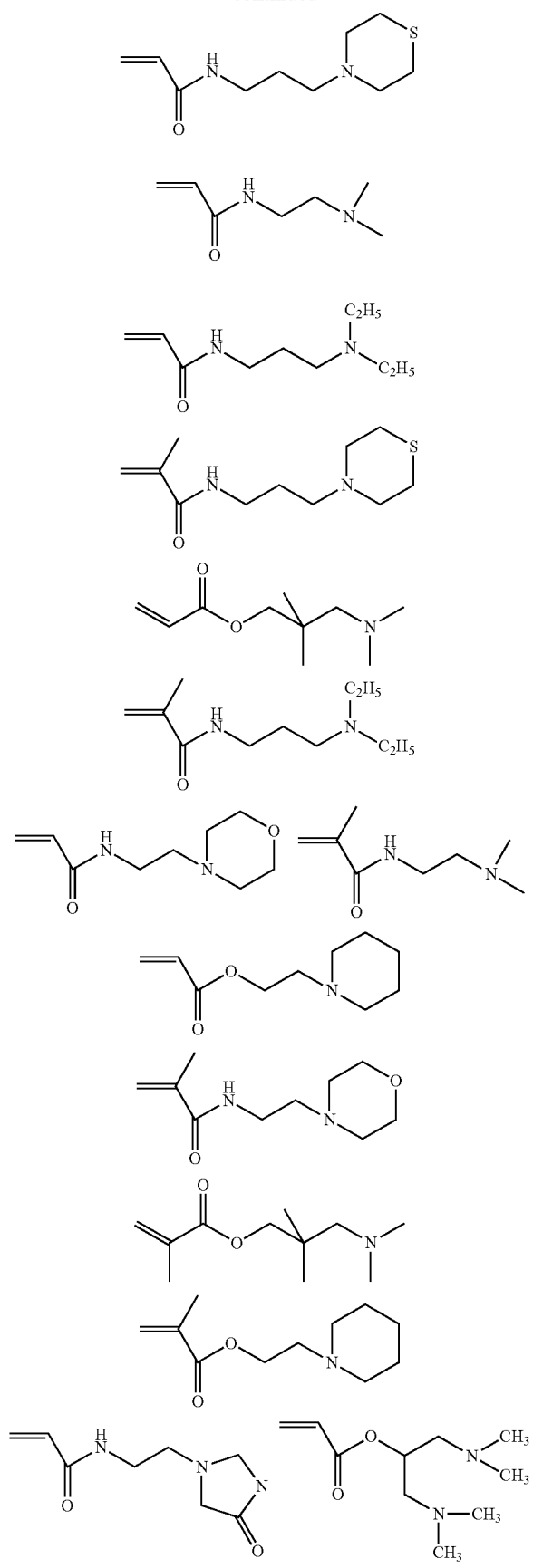
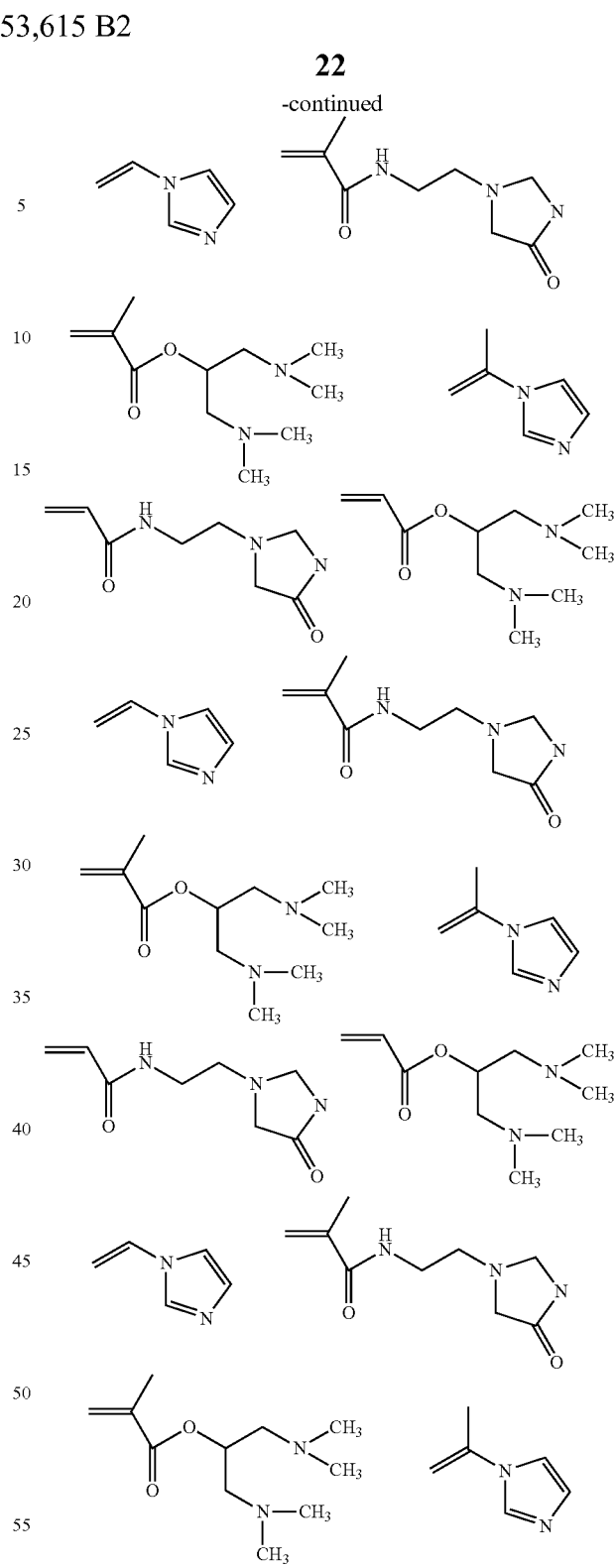

and also dimethylaminopropyl(meth)acrylamide, dimethylaminoethyl(meth)acrylamide, diethylaminoethyl(meth)acrylate, dimethylaminoethyl(meth)acrylate, vinylimidazole, vinylpyridine or morpholinoethyl(meth)acrylate.

20. The copolymer as claimed in claim 1, wherein the monomer of formula (III), alone or as a mixture, is present in a proportion of 2 to 30% by weight, with respect to the weight of the final copolymer.

21. The copolymer as claimed in claim 1, wherein the monomer of formula (II), alone or as a mixture, is present in a proportion of at least 6% by weight with respect to the weight of the final copolymer.

22. The copolymer as claimed in claim 1, in which, in the formula (I), n is 95 to 250.

23. The copolymer as claimed in claim 1, in which, in the formula (I), n is 100 to 200.

24. The copolymer as claimed in claim 1, wherein Y is —COOH.

25. The copolymer as claimed in claim 1, wherein the anionic monomer is chosen from, alone or as a mixture, acrylic acid and methacrylic acid.

26. The copolymer as claimed in claim 1, wherein the monomer of formula (I), alone as a mixture, is present in an amount of 70 to 95% by weight.

27. The copolymer as claimed in claim 1, wherein the monomer of formula (I), alone as a mixture, is present in an amount of 70 to 85% by weight.

28. The copolymer as claimed in claim 1, wherein the monomer of formula (I), alone as a mixture, is present in an amount of 65.5% by weight.

29. The copolymer as claimed in claim 1, wherein the monomer of formula (I), alone as a mixture, is present in an amount of 67.2% by weight.

30. The copolymer as claimed in claim 1, wherein the monomer of formula (I), alone as a mixture, is present in an amount of 72% by weight.

31. The copolymer as claimed in claim 1, in which, in the formula (I), n is between 90 and 300.

32. The copolymer as claimed in claim 1, in which, in the formula (I), n is between 100 and 300.

33. The copolymer as claimed in claim 1 wherein the monomer of formula (I) is polyethylene glycol methacrylate having a molecular weight of 5000 and is present in an amount of 67.2% by weight; the monomer of formula (II) is dimethylaminopropylmethacrylamide and is present in an amount of 20% by weight and the monomer of formula (III) is a mixture of methacrylic acid present in an amount of 2.8% by weight and acrylic acid present in an amount of 10% by weight.

34. The copolymer as claimed in claim 1 wherein the monomer of formula (I) is polyethylene glycol methacrylate having a molecular weight of 5000 and is present in an amount of 65.5% by weight; the monomer of formula (II) is dimethylaminopropylmethacrylamide and is present in an amount of 13.6% by weight and the monomer of formula (III) is a mixture of methacrylic acid present in an amount of 2.7% by weight and acrylic acid present in an amount of 18.2% by weight.

35. The copolymer as claimed in claim 1 wherein the monomer of formula (I) is polyethylene glycol methacrylate having a molecular weight of 5000 and is present in an amount of 72% by weight; the monomer of formula (II) is dimethylaminopropylmethacrylamide and is present in an amount of 25% by weight and the monomer of formula (III) is methacrylic acid present in an amount of 3% by weight.

36. A cosmetic method for treating keratinous substances, comprising the application to said substances of a cosmetic composition as defined in claim 10.

* * * * *